United States Patent
Cox et al.

(10) Patent No.: US 8,052,701 B1
(45) Date of Patent: Nov. 8, 2011

(54) METHOD AND APPARATUS FOR RUPTURING A VULNERABLE PLAQUE

(75) Inventors: Daniel L. Cox, Palo Alto, CA (US);
Jeffrey Ellis, San Francisco, CA (US);
Timothy A. Limon, Cupertino, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 72 days.

(21) Appl. No.: 10/453,116

(22) Filed: Jun. 2, 2003

(51) Int. Cl.
*A61B 17/32* (2006.01)

(52) U.S. Cl. ............ 606/159; 623/1.14; 606/170

(58) Field of Classification Search .......... 606/159; 604/164.1, 164.01, 164.03; 623/1.14
See application file for complete search history.

(56) References Cited

U.S. PATENT DOCUMENTS

| | | | | |
|---|---|---|---|---|
| 4,919,133 A | * | 4/1990 | Chiang | 606/159 |
| 4,976,711 A | * | 12/1990 | Parins et al. | 606/48 |
| 4,998,933 A | * | 3/1991 | Eggers et al. | 606/41 |
| 5,443,443 A | * | 8/1995 | Shiber | 604/22 |
| 5,554,163 A | * | 9/1996 | Shturman | 606/159 |
| 5,843,164 A | * | 12/1998 | Frantzen et al. | 623/1.16 |
| 5,972,019 A | * | 10/1999 | Engelson et al. | 606/200 |
| 6,168,579 B1 | * | 1/2001 | Tsugita | 604/96.01 |
| 6,331,191 B1 | * | 12/2001 | Chobotov | 623/1.44 |
| 6,419,659 B1 | | 7/2002 | Phelps et al. | |
| 6,450,964 B1 | | 9/2002 | Webler | |
| 6,451,044 B1 | | 9/2002 | Naghavi et al. | |
| 6,808,531 B2 | * | 10/2004 | Lafontaine et al. | 606/159 |
| 2002/0019627 A1 | * | 2/2002 | Maguire et al. | 606/27 |
| 2002/0161390 A1 | * | 10/2002 | Mouw | 606/200 |

* cited by examiner

*Primary Examiner* — Thomas J Sweet
*Assistant Examiner* — Christopher D Prone
(74) *Attorney, Agent, or Firm* — Blakely, Sokoloff, Taylor & Zafman LLP; Randy Shen

(57) ABSTRACT

Methods and apparatuses for treating a vulnerable plaque are described herein. In one aspect of the invention, the exemplary apparatus includes a medical device to treat a vulnerable plaque within a body lumen, where the medical device is adapted to position a rupturing device to rupture a fibrous cap of a vulnerable plaque. In one particular embodiment, the medical device includes a rupturing wire having a predetermined pattern to enable the rupturing device to rupture the fibrous cap of the vulnerable plaque. Other methods and apparatuses are also described.

31 Claims, 18 Drawing Sheets

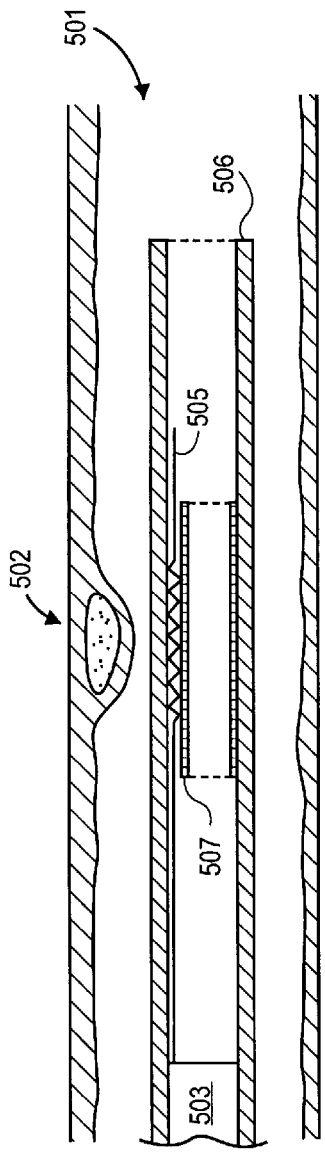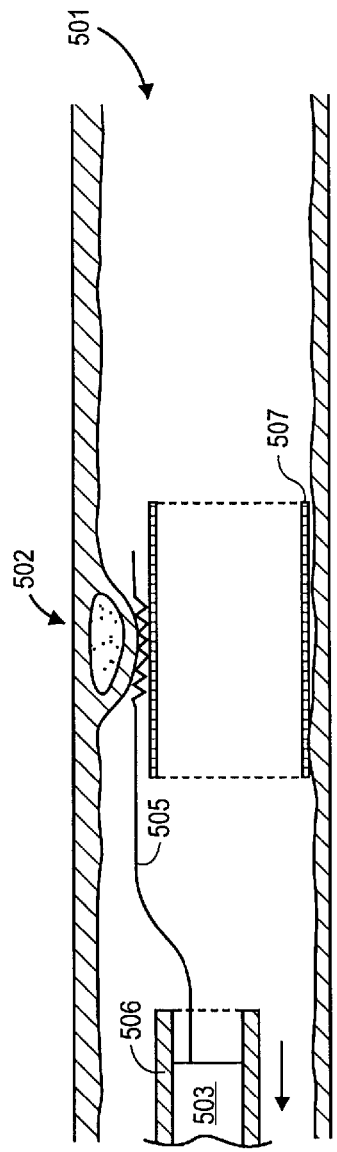
FIG. 5C
FIG. 5D

METHOD AND APPARATUS FOR RUPTURING A VULNERABLE PLAQUE

FIELD OF THE INVENTION

The present invention relates generally to the treatment of coronary disease, and more particularly, in one embodiment, to rupturing a fibrous cap of a vulnerable plaque.

BACKGROUND OF THE INVENTION

Coronary heart disease is generally thought to be caused by the narrowing of coronary arteries by atherosclerosis, which includes the buildup of fatty deposits in the lining of the arteries. The process that may lead to atherosclerosis begins with the accumulation of excess fats and cholesterol in the blood. These substances infiltrate the lining of arteries, gradually increasing in size to form deposits commonly referred to as plaque or atherosclerotic occlusions. Plaques narrow the arterial lumen and impede blood flow. Blood cells may collect around the plaque, eventually creating a blood clot that may block the artery completely.

The phenomenon of "vulnerable plaque" has created new challenges in recent years for the treatment of heart disease. Unlike occlusive plaques that impede blood flow, vulnerable plaque develops within the arterial walls, but it often does so without the characteristic substantial narrowing of the arterial lumen which produces symptoms. As such, conventional methods for detecting heart disease, such as an angiogram, may not detect vulnerable plaque growth into the arterial wall. After death, an autopsy can reveal the plaque congested in the arterial wall that could not have been seen otherwise with currently available medical technology.

The intrinsic histological features that may characterize a vulnerable plaque include increased lipid content, increased macrophage, foam cell and T lymphocyte content, and reduced collagen and smooth muscle cell (SMC) content. As shown in FIG. 1A, this fibroatheroma type of vulnerable plaque 101 is often referred to as "soft," having a large lipid pool 102 of lipoproteins surrounded by a fibrous cap 103. The fibrous cap 103 contains mostly collagen, whose reduced concentration combined with macrophage derived enzyme degradations can cause the fibrous cap of these lesions to rupture under unpredictable circumstances. When ruptured, as shown in FIG. 1B, the lipid core contents, thought to include tissue factor, contact the arterial bloodstream 104, causing a blood clot 105 to form that can completely and very quickly block the artery (e.g., lumen 106) resulting in an acute coronary syndrome (ACS) event. This type of atherosclerosis is coined "vulnerable" because of the unpredictable tendency of the plaque to rupture. It is thought that hemodynamic and cardiac forces, which yield circumferential stress, shear stress, and flexion stress, may cause disruption of a fibroatheroma type of vulnerable plaque. These forces may rise as the result of simple movements, such as getting out of bed in the morning, in addition to in vivo forces related to blood flow and the beating of the heart. It is thought that plaque vulnerability in fibroatheroma types is determined primarily by factors which include: (1) size and consistency of the lipid core; (2) thickness of the fibrous cap covering the lipid core; and (3) inflammation and repair within the fibrous cap.

Some physicians have stated that rupture of a vulnerable plaque during a PTCI (percutaneous transluminal coronary intervention) is desirable. The rationale is that if a rupture is going to occur, it is better to have it happen in the safety and security of the catheterization lab. In this way, an immediate corrective action can be taken to deal with the plaque rupture. It has been further stated that it may be desirable to have the lipid pool under the fibrous cap completely drained to prevent a blood clot build up. Therefore, it is desirable to have a device which will ensure rupture of the fibrous cap during the intervention.

SUMMARY OF THE INVENTION

Methods and apparatuses for treating a vulnerable plaque are described herein. In one aspect of the invention, the exemplary apparatus includes a medical device to treat a vulnerable plaque within a body lumen, where the medical device is adapted to position a rupturing device to rupture a fibrous cap of a vulnerable plaque. In one particular embodiment, the medical device includes a rupturing wire having a predetermined pattern to enable the rupturing device to rupture the fibrous cap of the vulnerable plaque.

According to another aspect of the invention, an exemplary catheter capable of treating a vulnerable plaque includes a rupturing device having a predetermined shape extending from a distal end of the catheter and an expandable device extending from the distal end of the catheter. When expanded, the expandable device positions the rupturing device against a vulnerable plaque to rupture a fibrous cap of the vulnerable plaque. In one particular embodiment, the rupturing device is pulled to rupture the fibrous cap of the vulnerable plaque while the expandable device maintains a stress concentration between the rupturing device and the vulnerable plaque.

The present invention also includes other apparatuses and methods to operate these apparatuses. Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings in which like references indicate similar elements.

FIGS. 5C and 5D are diagrams illustrating an exemplary process to treat a vulnerable plaque according to yet another embodiment of the invention.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Accordingly, apparatuses and methods are provided to rupture a fibrous cap of a vulnerable plaque. According to one embodiment, a rupturing device, such as a rupturing wire, when placed against the vulnerable plaque, is used to rupture a fibrous cap of the vulnerable plaque. In one embodiment, a rupturing device ruptures the fibrous cap by forming stress concentrations on the fibrous cap. As a result, the fibrous cap of the vulnerable plaque is ruptured. In an alternative embodiment, the rupturing device is designed with a predefined shape or pattern. The rupturing device is then pulled to rupture the fibrous cap while it is held in contact with the fibrous cap by an expandable device, such as, for example, a balloon or a stent. As a result, the friction on the fibrous cap during pulling tears the fibrous cap open.

The simplest design of a predefined pattern is a straight wire. When placed on a vulnerable plaque with stress concentration, the wire ruptures a fibrous cap of the vulnerable plaque. Alternatively, a serpentine shape wire which stretches open during pulling enhances rupturing the fibrous cap. Further, a pattern with one or more protrusions orthogonal to each other may be used. Further, a pattern with a series of stress concentrations along a wire may be used. Furthermore, the rupturing device may include one or more sharp members, which may be made from wire, or cut from a flat or curved sheet or tube to provide a sharp edge, to rupture a fibrous cap of a vulnerable plaque. Stress concentrations and serpentine shapes may be combined to form a rupturing device. Alternatively, one or more closed cells along a wire which open during pulling may be used. It is preferable in some embodiments to use a rupturing device with a balloon catheter during a pretreatment. In addition, an intra-vascular ultrasonic (IVUS) system or an optical coherent tomography (OCT) system may be used to monitor the rupturing device and the fibrous cap during rupturing. The magnitudes of protrusions or amplitudes of the serpentine patterns may be made according to a degree of tearing desired.

Figure 1A:
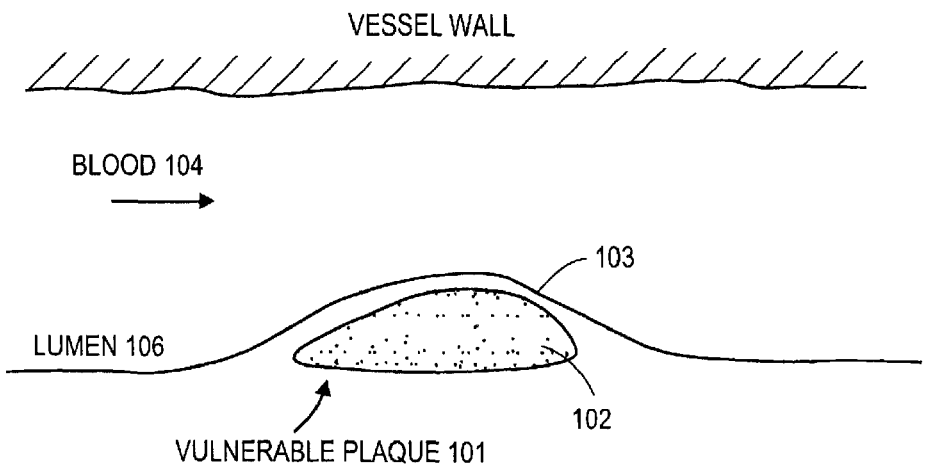
FIGS. 1A and 1B show a typical vulnerable plaque having a fibrous cap and a lipid pool underneath the fibrous cap.
Figure 1B:
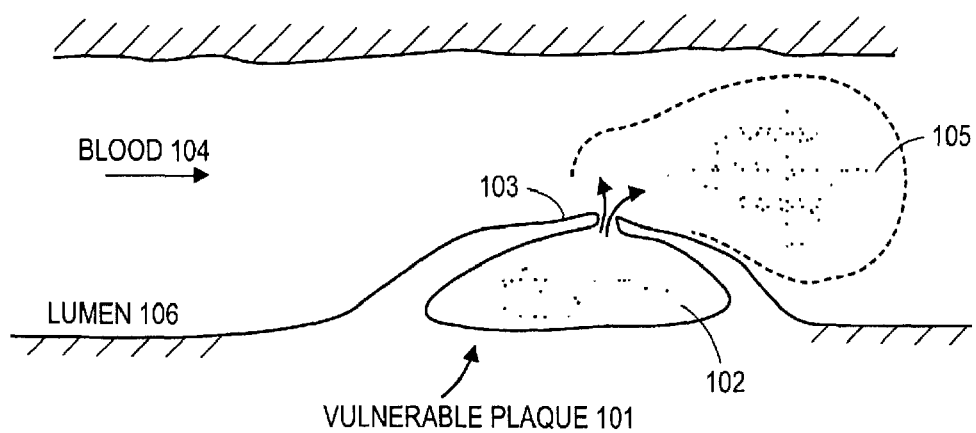
Figure 2:
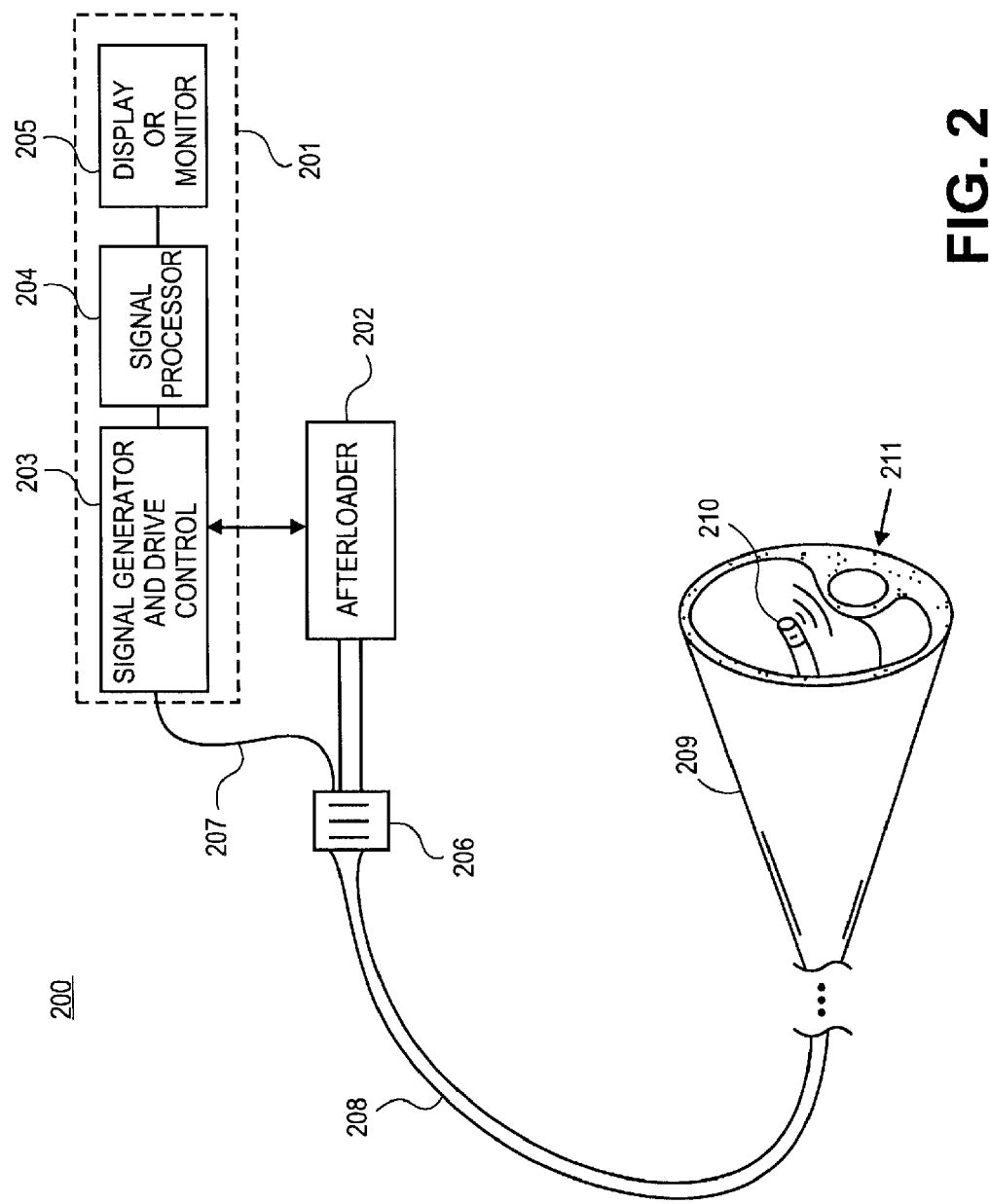
FIG. 2 is a block diagram illustrating an exemplary system for treating a vulnerable plaque in accordance with one embodiment of the invention.

FIG. 2 illustrates a simplified block diagram of a system to rupture a fibrous cap of a vulnerable plaque in accordance with an embodiment of the invention. Referring to FIG. 2, according to one embodiment, the system 200 includes an imaging system 201 (such as, for example, an IVUS or OCT system), an afterloader system 202, and a catheter system 208. The imaging system 201 includes a signal generator/ drive control 203, a signal processor 204, and a display/ monitor 205. The signal generator/drive control 203 is operatively connected to the rotary drive 206 and the ultrasonic transducer in a distal end 210 of the catheter system 208 by an electrical connector/cable 207. An electrical wire may be extended through the catheter shaft to connect the ultrasonic transducer in the distal end 210 to the cable 207.

The imaging system 201 may be an intra-vascular ultrasonic (IVUS) system commercially available. The IVUS is commonly performed as an adjunctive imaging modality following coronary angiography. This technique is particularly useful in guiding radiation therapy. The ultrasound image is cross-sectional in nature and is also a full motion display of the cross-sectional appearance of the vessel. The IVUS image is produced by advancing a catheter within the vessel that sends and receives ultrasound signals generated via a transducer. An image processing computer reconstructs the full cross-sectional image on the received ultrasound information. Alternatively, according to another embodiment, an optical coherent tomography (OCT) imaging system may be used in place of IVUS system 201.

In one embodiment, the catheter system 208 includes an elongated shaft having a distal end 210. The distal end 210 may include an ultrasonic transducer (not shown) to transmit and receive ultrasonic signals. In addition, the distal end 210 may include a rupturing device to rupture a fibrous cap of a vulnerable plaque 211 in a blood lumen 209. Furthermore, an expandable device, such as a balloon, may be disposed at the distal end 210. The expandable device, when expanded, positions the rupture device against the vulnerable plaque. As a result, a stress concentration is created on the vulnerable plaque which in turn ruptures the fibrous cap of the vulnerable plaque. In one embodiment, the fibrous cap is ruptured when the rupturing device along with the expandable device is pulled while maintaining the stress concentration. Alternatively, the rupturing device may be pulled to rupture the fibrous cap while the expandable device remains steady to maintain the stress concentration. The imaging system 201 may be used to monitor the rupturing device and the vulnerable plaque during the rupturing. In one embodiment, the rupturing device includes a wire having a predefined shape including, for example, a serpentine shape, or one or more protrusions orthogonal to each other, or a series of stress concentrations along the wire, or a serrate pattern along the wire, or a serpentine shape with a series of stress concentrations, or one or more closed cells along the wire. Optionally, according to one embodiment, an afterloader 202 may be used to advance and retract a wire into and out from the catheter system 208. The afterloader 202 may be commercially available, for example, from Guidant Corporation.

Figure 3A:
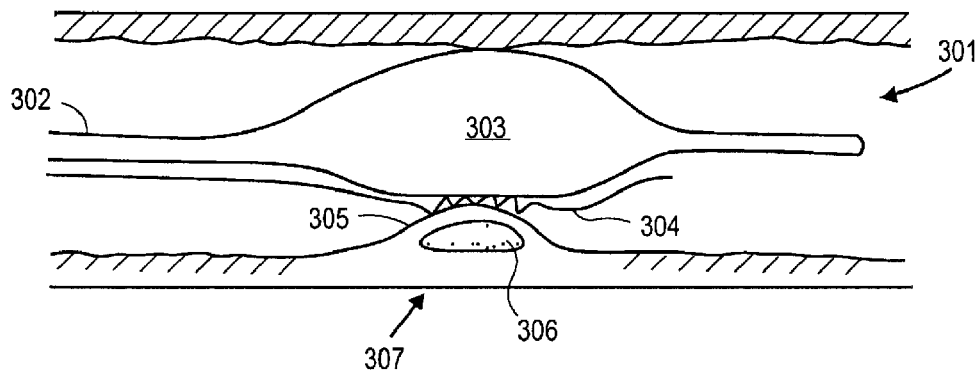
FIGS. 3A to 3D are diagrams illustrating an exemplary process to treat a vulnerable plaque according to one embodiment of the invention.

FIGS. 3A to 3D are diagrams illustrating a process of rupturing a fibrous cap of a vulnerable plaque according to one embodiment of the invention. Referring to FIG. 3A, once a vulnerable plaque 307 is detected in a body lumen 301, a catheter is inserted into the body lumen 301. The body lumen may be a coronary artery or other vessel with a vulnerable plaque. The catheter may be similar to a conventional PTCI catheter such as one used for balloon angioplasty. A catheter would typically include, at least in certain embodiments, a balloon, deployable at a distal end of the catheter, where the balloon is coupled to a balloon lumen in order to inflate the balloon with an inflation fluid through the balloon lumen. The balloon lumen is coupled at a proximal end of the catheter to a source of the inflation fluid and is disposed within a larger lumen formed by the catheter. The catheter also may include a guide wire lumen which allows for the introduction of a guide wire into the guide wire lumen. The guide wire is used to position the catheter with a vessel, as is known in the art. The guide wire may be a conventional guide wire. The catheter may also include a lumen which is used to introduce a fluid (e.g. heparinized saline) into the blood vessel during the rupturing or after the rupturing of the vulnerable plaque. Typically, the vulnerable plaque 307 may include a relatively thin fibrous cap 305 and a relatively large lipid pool 306 underneath. In one embodiment, the vulnerable plaque 307 may be detected via an imaging system, such as an IVUS system or an OCT system. Since a temperature of a vulnerable plaque is normally warmer than the normal tissues, the vulnerable plaque 307 may be detected by measuring the temperature of the vulnerable plaque. Alternatively, the vulnerable plaque 307 may be detected by measuring a changing rate of the temperature after altering the temperature of the vulnerable plaque to a predetermined temperature. The temperature of the vulnerable plaque may be altered by flushing a warm or cold fluid having a predetermined temperature to the respective region. The temperature of the vulnerable plaque 307 may be detected via one or more thermal sensors deployed from a distal end 302 of the catheter. In one embodiment, a flow deflector may be attached to each of the thermal sensors to deflect a blood flow away from the vulnerable plaque while the temperature is detected to improve the accuracy of the measurement. The imaging system and rupture system (e.g., rupturing device and balloon/stent) may be separate devices. In one embodiment, the OCT system may include an image wire having a diameter around 0.014 inches within a catheter. Other configurations may be utilized.

As shown in FIG. 3A, once the catheter is inserted into the lumen 301 near the vulnerable plaque 307, a rupturing device 304 is deployed and positioned against the vulnerable plaque 307 to rupture fibrous cap 305 of the vulnerable plaque 307. In one embodiment, an expandable device 303 is also deployed along with the rupturing device 304. The expandable device 303, when expanded, positions the rupturing device 304 against the fibrous cap 305 of the vulnerable plaque 307. According to one embodiment, the expandable device 303, when expanded, creates a stress concentration between the rupturing device 304 and the fibrous cap 305. As a result, the stress concentration built up between the rupturing device 304 and the fibrous cap 305 is strong enough to rupture the fibrous cap 305 of the vulnerable plaque 307.

In one embodiment, the expandable device 303 is a balloon. The balloon 303 may be part of a separate balloon catheter or integrated with a catheter suitable for IVUS or OCT measurements, extended from a distal end 302 of a catheter. According to another embodiment, the rupturing device may be integrated into an atherectomy catheter in place of a cutter therein. Such atherectomy catheter may be available from Guidant Corporation. Further detailed information concerning an atherectomy catheter can be found in U.S. patent application Ser. No. 09/312,076, which is assigned to the common assignee of the present application, and which is hereby expressly incorporated by reference. The balloon 303, when inflated, positions the rupturing device 304 against the fibrous cap 305 of the vulnerable plaque 307 and creates a stress concentration between the rupturing device 304 and the fibrous cap 305 of the vulnerable plaque 307. Other devices, such as a stent, may be used to hold the rupturing device 304 against the fibrous cap 305 of the vulnerable plaque 307 to enable the rupturing device 304 to rupture the fibrous cap 305 of the vulnerable plaque 307.

Figure 3B:
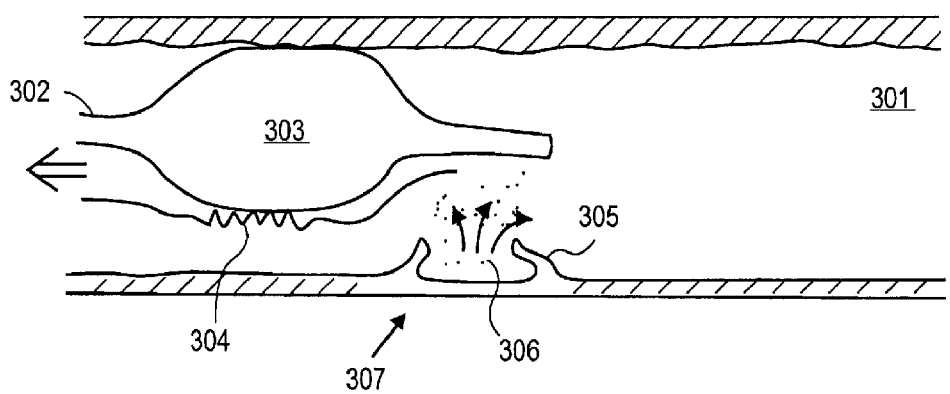

According to another embodiment, if the stress concentration built up between the rupturing device 304 and the fibrous cap 305 of the vulnerable plaque 307 is not strong enough, the fibrous cap 305 may be ruptured by pulling both the expanded device 303 and the rupturing device 304, as shown in FIG. 3B, while maintaining the stress concentration. In this embodiment, the rupturing is accomplished by a combination of both stress concentrations built up by the expanded device 303 on a vertical orientation and tearing forces caused by the pulling on a horizontal orientation, as shown in FIG. 3B.

In one embodiment, the stress concentration may be adjusted by a force to expand the expandable device 303. In a case of a balloon, the balloon may be inflated via a liquid, such as saline, contrast media, or contrast media diluted with saline. Alternatively, the balloon may be inflated via a gas such as carbon dioxide ($CO_2$). The stress concentration may be adjusted by the pressure to inflate the balloon. The pressure may be controlled via a pressure controller connected via a proximal end of the catheter, which may be a part of the system 200 illustrated in FIG. 2.

Figure 3C:
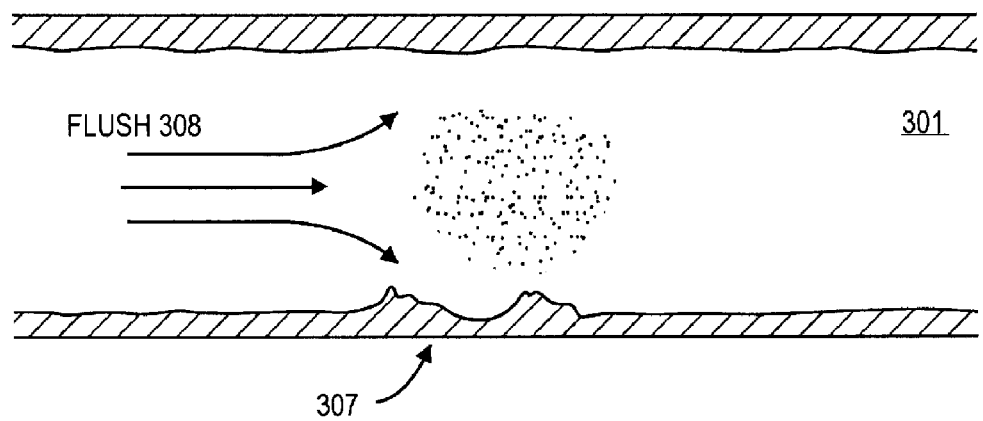
Figure 3D:
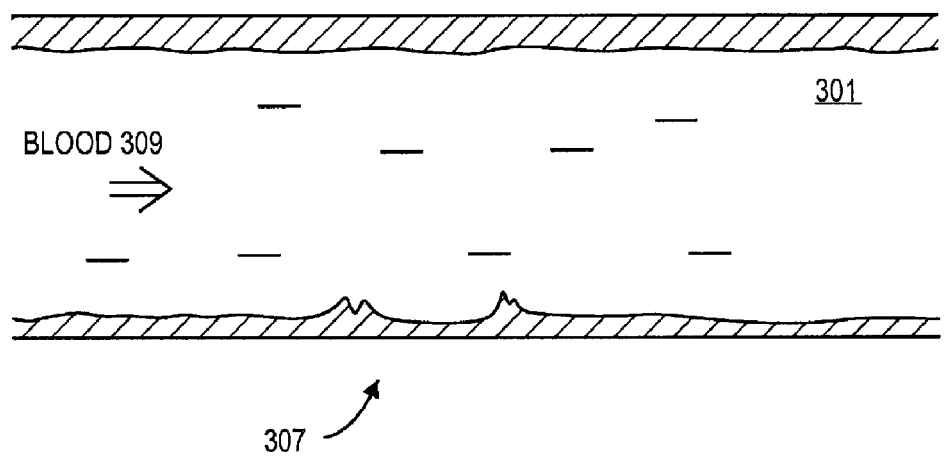

After the fibrous cap 305 is ruptured via a process disclosed by one of the above embodiments, the contents of the lipid pool 306 are leaked into the lumen 301. The contents of the lipid pool 306 may include tissue factor, which when contacting the bloodstream, would cause a blood clot to form that can completely block the lumen 301 resulting in an acute coronary syndrome (ACS) event. As a result, during a pretreatment, it is desirable to remove or completely drain the contents of the lipid pool 306 to prevent such blood clots from being built up. According to one embodiment, after the fibrous cap 305 is ruptured, as shown in FIG. 3C, a fluid 308 is infused into the lumen 301 to flush out the contents of the lipid pool 306 leaking into the lumen 301. As a result, as shown in FIG. 3D, when a bloodstream 309 is restored, no blood clot is formed to block the lumen 301. In one embodiment, a liquid, such as saline, may be used to flush the contents of the lipid pool 306 out of the lumen 301. According to one embodiment, heparinized saline may be used to flush out the contents of the lipid pool via the guiding catheter. Alternatively, a lumen may be included within the catheter for flushing purposes.

Figure 3E:
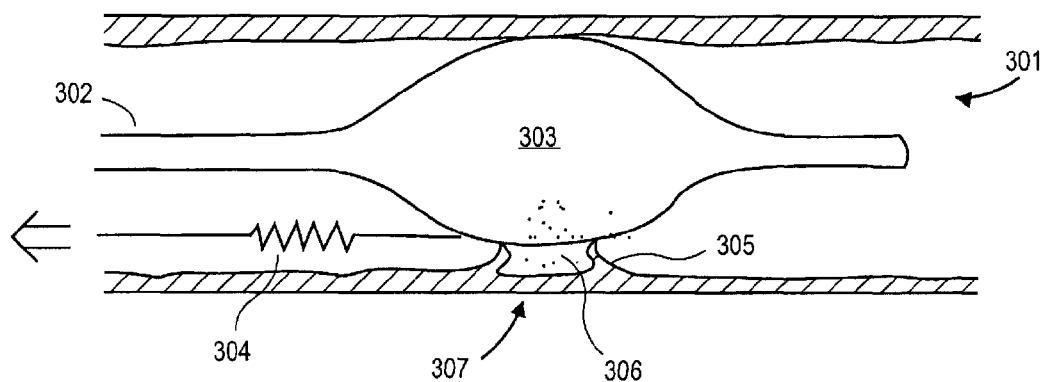
FIG. 3E is a diagram illustrating an exemplary process to treat a vulnerable plaque according to an alternative embodiment of the invention.

According to another embodiment, as shown in FIG. 3E, when the rupturing device 304 is pulled to rupture the fibrous cap 305 of vulnerable plaque 307, the expandable device 303 may remain steady to continue to provide stress concentration between the rupturing device 304 and the vulnerable plaque 307. However, a caution may be taken that the pulling of the rupturing device 304 would not rupture the expandable device 303, particularly, when the expandable device is a balloon. The materials used to make the expandable device 303 and the rupturing device 304 may be selected by taking into consideration such configuration. Alternatively, the shapes or patterns of the rupturing device 304 may be adjusted to work under such circumstances. In one embodiment, the rupturing device 304 includes a wire having a predefined shape or pattern as shown in FIGS. 8A to 8J, which will be described in detail further below.

Figure 4A:
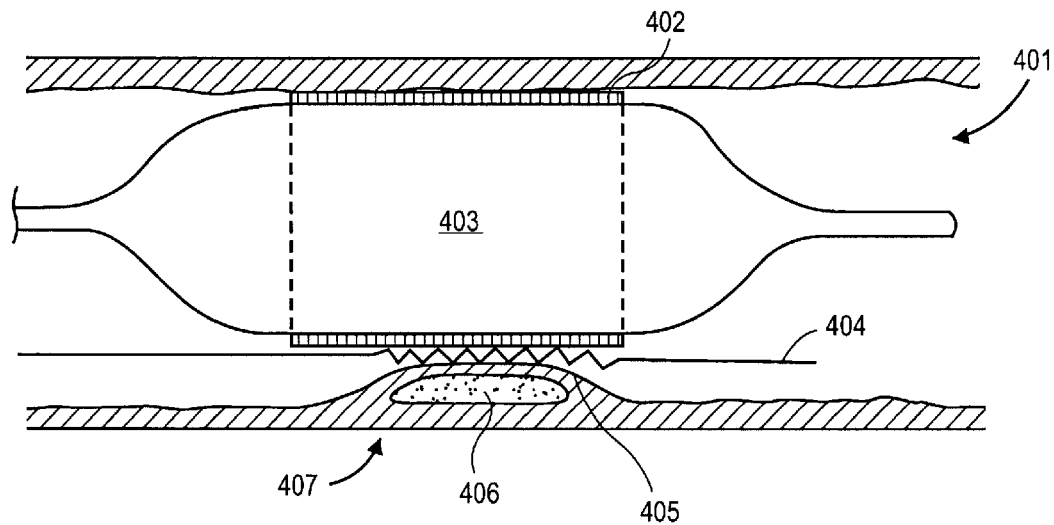
FIGS. 4A and 4B are diagrams illustrating an exemplary process to treat a vulnerable plaque according to another embodiment of the invention.
Figure 4B:
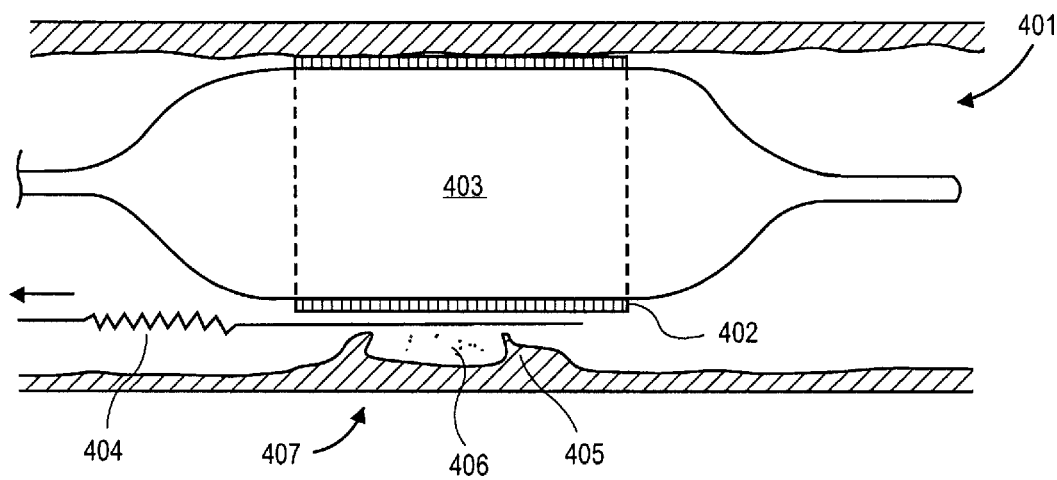

FIGS. 4A and 4B are diagrams illustrating a rupturing process in accordance with another embodiment of the invention. In this embodiment, after vulnerable plaque 407 is detected via one of the above methods or other methods, rupturing of fibrous cap 405 of the vulnerable plaque 407 may be performed during a stenting procedure. As shown in FIG. 4A, a stent 402 is delivered, through a catheter, into the lumen 401 near the vulnerable plaque 407 after the vulnerable plaque 407 is detected via one of the aforementioned methods. During the delivery, a rupturing device 404 is also delivered along the stent 402. The rupturing device 404 is positioned between the stent 402 and the vulnerable plaque 407. The stent 402 is then deployed by a balloon extended from a distal end of a catheter. When the stent 402 is deployed, it forces the rupturing device 404 against the fibrous cap 405 of vulnerable plaque 407, which in turn creates a stress concentration at the contacting point between the rupturing device 404 and the vulnerable plaque 407. According to one embodiment, the stress concentration is strong enough to force the rupturing device 404 to rupture the fibrous cap 405 of the vulnerable plaque 407.

According to another embodiment, if the stress concentration is not strong enough to rupture the fibrous cap 405, as shown in FIG. 4B, the rupturing device 404 may be pulled to rupture the fibrous cap, while the stent 402 and the balloon 403 remain steady to maintain the stress concentration. In this embodiment, the rupturing is accomplished by a combination of both stress concentrations built up by the balloon 403 and the stent 402 on a vertical orientation and tearing forces caused by pulling the rupturing device 404 on a horizontal orientation. However, caution should be taken to ensure that the pulling of the rupturing device 404 would not disrupt the structure of stent 402 and balloon 403.

Figure 4C:
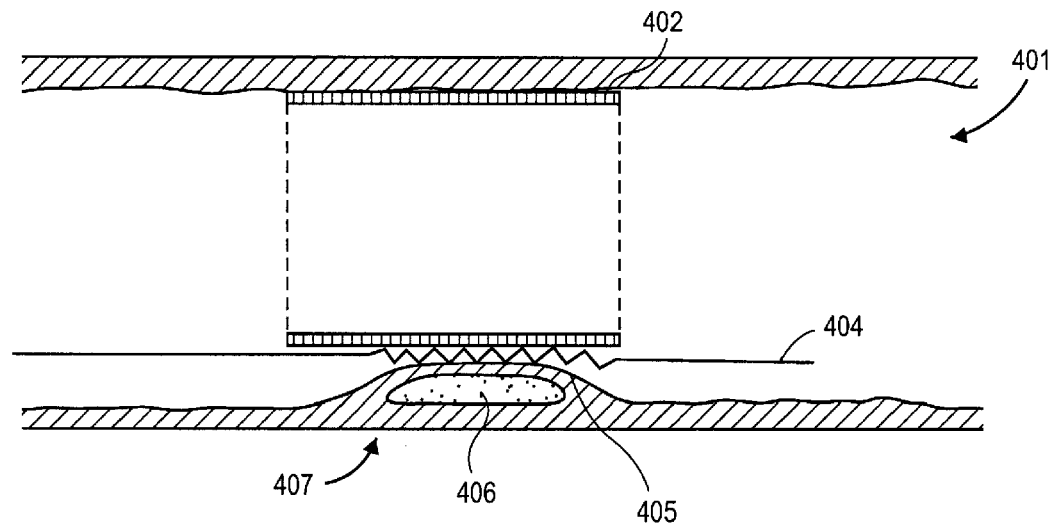
FIGS. 4C and 4D are diagrams illustrating an exemplary process to treat a vulnerable plaque according to another embodiment of the invention.
Figure 4D:
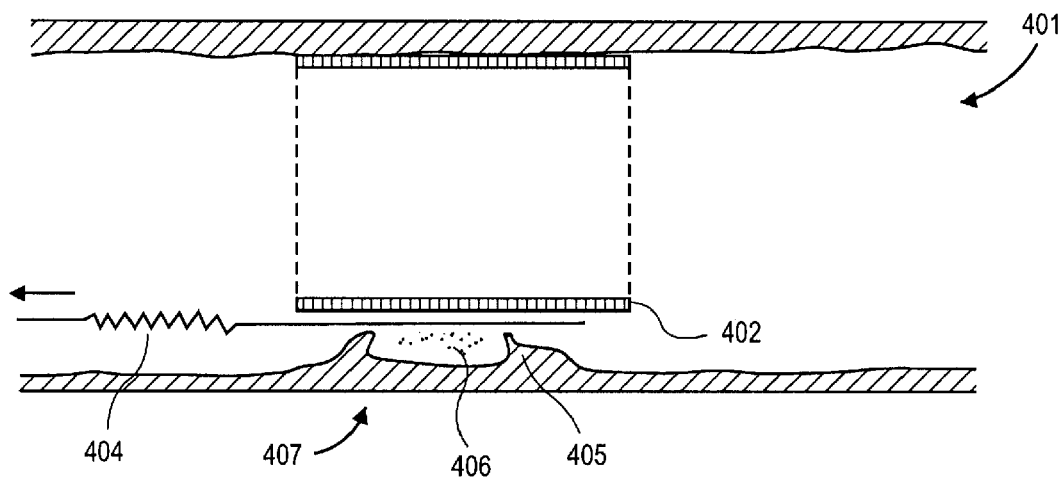

FIGS. 4C and 4D are diagrams illustrating a rupturing process in accordance with another embodiment of the invention. In this embodiment, after stent 402 and rupturing device 404 have been delivered and stent 402 has been deployed by balloon 403 in FIG. 4A, balloon 403 may be withdrawn, as shown in FIG. 4C, while stent 402 is still expanded pushing rupturing device 404 against fibrous cap 405 of vulnerable plaque 407 which creates a stress concentration between rupturing device 404 and fibrous cap 405. In one embodiment, the stress concentration built up may be strong enough to rupture fibrous cap 405 of vulnerable plaque 407. Alternatively, rupturing device 404 may be pulled, via a predefined shape of the rupturing device, to rupture fibrous cap 405 of vulnerable plaque 407 while stent 402 is still expanded to provide the stress concentration. As a result, the pulling of rupturing device 404 does not disrupt the structure of balloon 403.

Figure 8B:
FIGS. 8A to 8I are diagrams illustrating exemplary rupturing devices in accordance with embodiments of the invention.
Figure 8D:
Figure 8A:
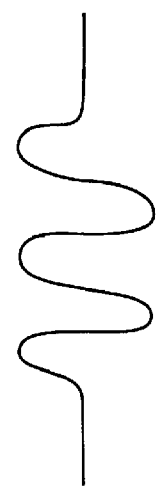
Figure 8C:
Figure 8F:
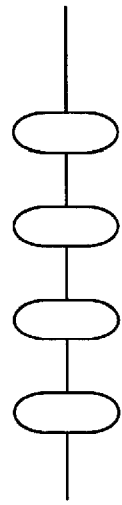
Figure 8I:
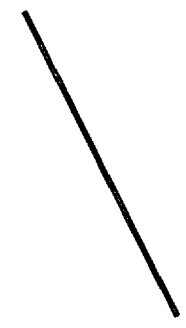
Figure 8H:
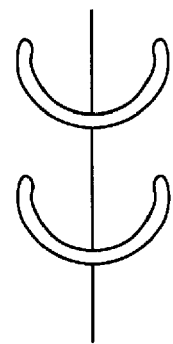
Figure 8E:
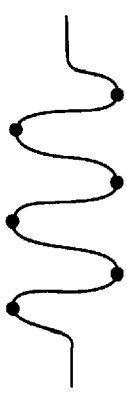
Figure 8G:
Figure 8J:
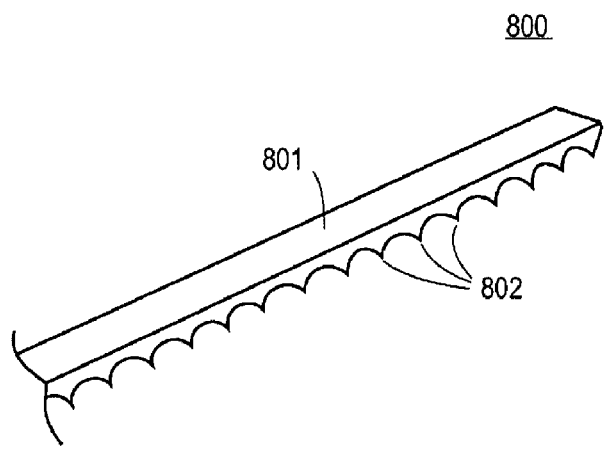
FIGS. 8J and 8K are diagrams illustrating exemplary rupturing devices in accordance with one embodiment of the invention.
Figure 8K:
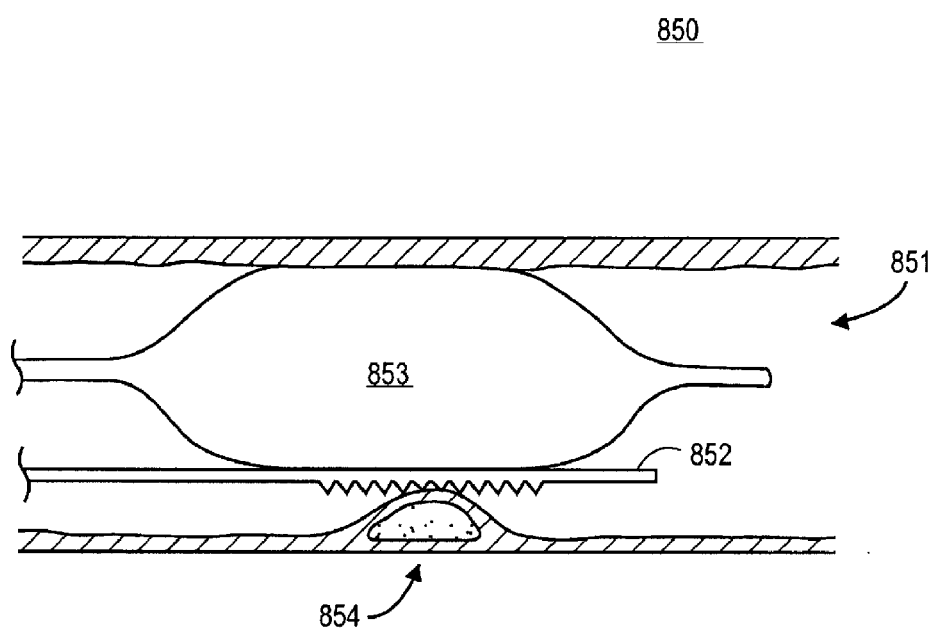

Alternatively, a rupturing device having a substantially smooth surface and a sharp edge, such as, for example, a rupturing device shown in FIGS. 8J and 8K, may be utilized. When such rupturing device is used, an expandable device, such as a balloon or a stent may be expanded to push on the smooth surface of the rupturing device and to position the sharp edge of the rupturing device against the fibrous cap of the vulnerable plaque. As a result, the smooth surface of the rupturing device may prevent the balloon or the stent from being disrupted.

In one embodiment, the stress concentration may be adjusted by a force to inflate the balloon 403. The balloon 403 may be inflated via a liquid, such as saline, contrast media, or contrast media diluted with saline. Alternatively, balloon 403 may be inflated via a gas such as carbon dioxide ($CO_2$). The stress concentration may be adjusted by a pressure to inflate the balloon. The pressure may be controlled via a pressure controller connected via a proximal end of the catheter, which may be a part of the system 200 shown in FIG. 2.

According to one embodiment, after the fibrous cap 405 is ruptured, a fluid may be infused into the lumen 401 to flush out the contents of the lipid pool leaking into the lumen 401, via one of the aforementioned methods, to prevent a blood clot from forming. In one embodiment, a liquid, such as saline, may be used to flush the contents of the lipid pool 406 out of the lumen 401. In a particular embodiment, heparinized saline may be used to flush out the contents of the lipid pool via the guiding catheter. Furthermore, a lumen may be included within the catheter for flushing purposes.

Figure 5A:
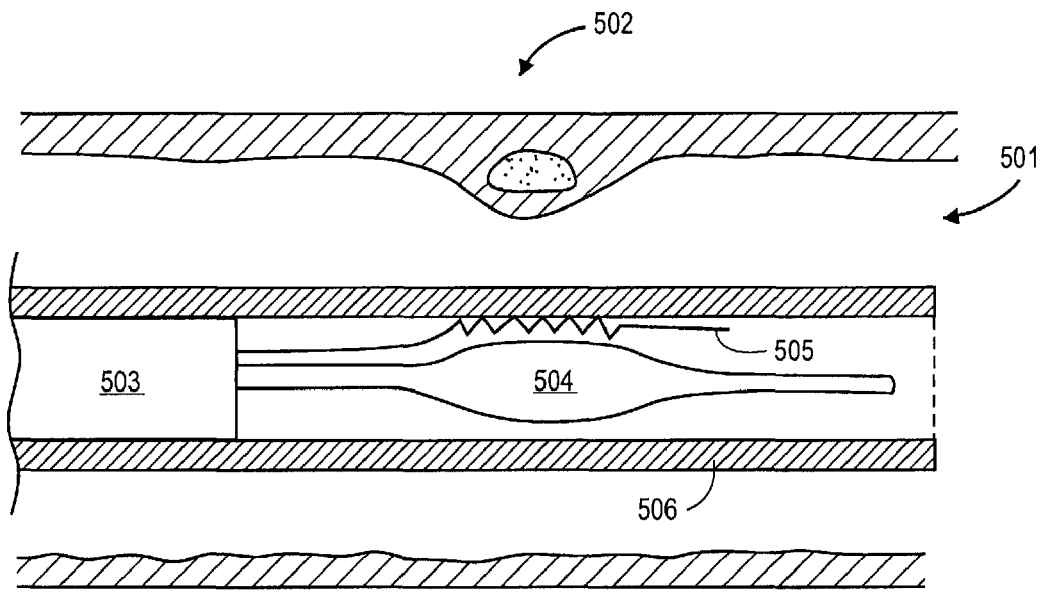
FIGS. 5A and 5B are diagrams illustrating an exemplary process to treat a vulnerable plaque according to yet another embodiment of the invention.
Figure 5B:
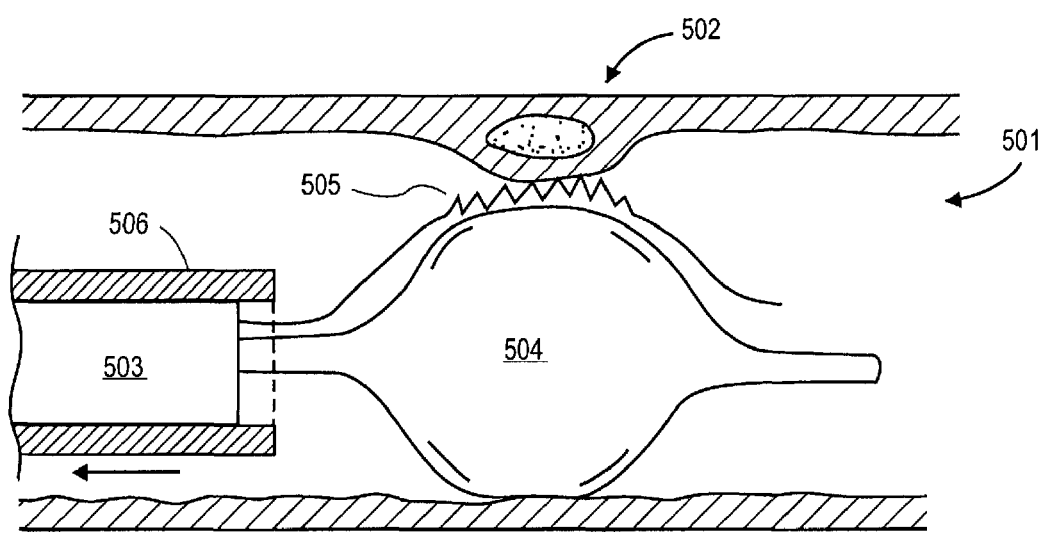

FIGS. 5A and 5B are diagrams illustrating an exemplary configuration of a medical device having a rupturing device in accordance with one embodiment of the invention. Referring to FIG. 5A, in one embodiment, the rupturing device 505 and an expandable device, such as a balloon 504 are extended from a distal end 503 of a catheter. According to one embodiment, the rupturing device 505 and balloon 504 are encapsulated by a retractable sheath 506 during a positioning of the distal end 503 within a lumen 501 near the vulnerable plaque 502. The vulnerable plaque 502 may be detected via one of the aforementioned methods including, for example, a temperature measurement. According to one embodiment, the positioning may be monitored via an IVUS or an OCT system which is part of the catheter.

After the balloon 504 and the rupturing device 505 are delivered to a location near the vulnerable plaque 502, as shown in FIG. 5B, the retractable sheath 506 is retracted to expose the rupturing device 405 and the balloon 504 to the region. The balloon 504 is then inflated to position the rupturing device 505 against a fibrous cap of the vulnerable plaque 502. The balloon 504 may be inflated by pumping a liquid, such as saline, contrast media, or contrast media diluted with saline, into the balloon through a pressure controller (not shown) coupled to a proximal end of the catheter. Alternatively, a gas, such as carbon dioxide ($CO_2$), may be used to inflate the balloon 504. Furthermore, the balloon 504 may be inflated automatically when the retractable sheath 506 is retracted. According to one embodiment, as shown in FIG. 5B, the inflated balloon 504 positions and forces the rupturing device 505 against the fibrous cap of the vulnerable plaque 502. As a result, a stress concentration is created between the rupturing device 505 and the vulnerable plaque 502. According to one embodiment, the stress concentration may be strong enough, via the rupturing device 505, to rupture the fibrous cap of the vulnerable plaque 502. Alternatively, as described above, the inflated balloon 504 and the rupturing device 505 may be pulled to rupture the fibrous cap of the vulnerable plaque 502. Furthermore, the rupturing device 505 may be pulled to rupture the fibrous cap while the inflated balloon remains steady to maintain the stress concentration between the rupturing device 505 and the vulnerable plaque 502.

FIGS. 5C and 5D are diagrams illustrating an exemplary configuration of a medical device having a rupturing device in accordance with another embodiment of the invention. Referring to FIG. 5C, in one embodiment, the rupturing device 505 and an expandable device, such as a stent 507 are extended from a distal end 503 of a catheter. In this embodiment, stent 507 may be a self-expandable stent, such that a balloon is not needed. According to one embodiment, rupturing device 505 and stent 507 are encapsulated by a retractable sheath 506 during positioning of the distal end 503 within a lumen 501 near the vulnerable plaque 502. The vulnerable plaque 502 may be detected via one of the aforementioned methods including, for example, a temperature measurement. According to one embodiment, the positioning may be monitored via an IVUS or an OCT system which is part of the catheter.

After stent 507 and the rupturing device 505 are delivered to a location near the vulnerable plaque 502, as shown in FIG. 5D, the retractable sheath 506 is retracted to expose the rupturing device 405 and stent 507 to the region. The stent 507 is then self-expanded to position the rupturing device 505 against a fibrous cap of the vulnerable plaque 502. According to one embodiment, as shown in FIG. 5D, the expanded stent 507 positions and forces the rupturing device 505 against the fibrous cap of the vulnerable plaque 502. As a result, a stress concentration is created between the rupturing device 505 and the vulnerable plaque 502. According to one embodiment, the stress concentration may be strong enough, via the rupturing device 505, to rupture the fibrous cap of the vulnerable plaque 502. Alternatively, according to one embodiment, rupturing device 505 may be pulled to rupture the fibrous cap while the expanded stent 507 remains steady to maintain the stress concentration between the rupturing device 505 and the vulnerable plaque 502.

According to one embodiment, in order not to disrupt the structure of stent 507, a rupturing device having a substantially smooth surface and a sharp edge, such as, for example, a rupturing device shown in FIGS. 8J and 8K, may be utilized. When such rupturing device is used, stent 507 may be expanded to push on the smooth surface of the rupturing device and to position the sharp edge of the rupturing device against the fibrous cap of the vulnerable plaque. As a result, the smooth surface of the rupturing device may prevent the structure of stent 507 from being disrupted. This is an example of a rupturing device which has sharp edges or members only facing a limited circumferential angle of the vessel (rather than a full 360° of the circumference of the vessel).

Figure 6A:
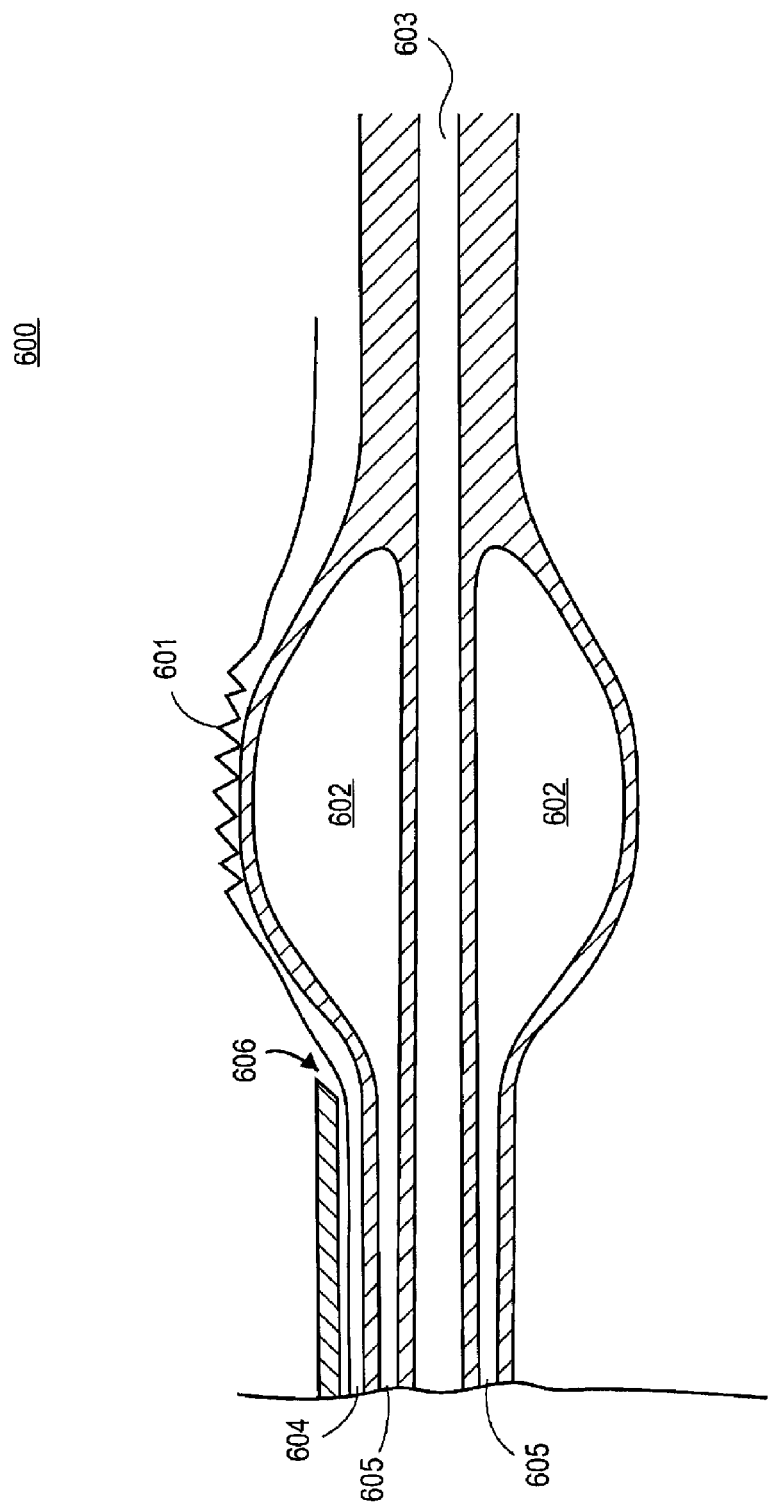
FIGS. 6A and 6B are diagrams illustrating an exemplary apparatus to treat a vulnerable plaque according to one embodiment of the invention.

According to another embodiment, as shown in the cross sectional view of FIG. 6A, a rupturing device lumen is extended along an inflation lumen and exits via a port near a balloon and is positioned around the balloon. Referring to FIG. 6A, in one embodiment, an exemplary distal end of a catheter 600 includes a rupturing device 601, a balloon 602, and a central lumen or a guide wire lumen 603. The rupturing device 601 is extended through a rupturing device lumen 604 and exits via a port 606. The rupturing device 601 exiting from port 606 goes around the balloon 602. The rupturing device lumen 604 is extended parallel to the inflation lumen 605 and the central lumen 603. When the balloon 602 is inflated, it positions the rupturing device 601 against a fibrous cap of a vulnerable plaque and creates a stress concentration between the rupturing device 601 and the vulnerable plaque which in turn may rupture the fibrous cap of the vulnerable plaque. Alternatively, both the balloon 602 and the rupturing device 601 may be pulled to rupture the fibrous cap of the vulnerable plaque while the inflated balloon maintains the desired stress concentration. A further lumen, not shown, may be disposed either in the same catheter and also have an exit port, near exit port 606, near the distal end of the catheter and have a proximal end which is coupled to receive a fluid (e.g. heparinized saline) which may be used to flush away the contents of the vulnerable plaque as it is being ruptured or after it is ruptured.

Figure 6B:
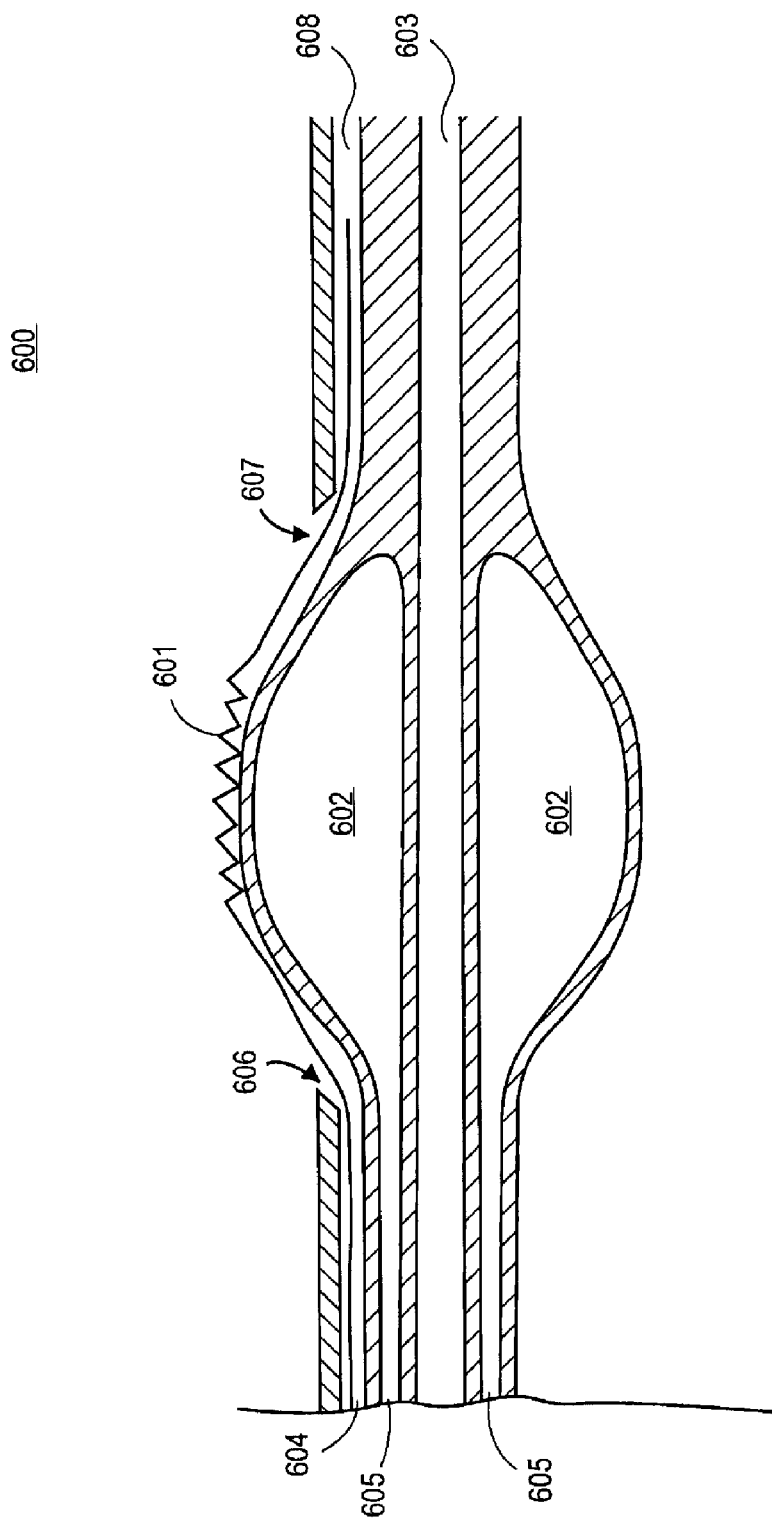

According to a further embodiment, as shown in the cross sectional view of FIG. 6B, the exemplary distal end of a catheter 600 includes a second rupturing device lumen 608 and a second port 607. As a result, the rupturing device 601 is extended from a first rupturing device lumen 604 and exits via a first port 606. The rupturing device 601 goes around the body of the balloon 602. The rupturing device 601 then goes into a second rupturing device lumen 608 via a second port 607. As a result, both first and second lumens 604 and 608 retain the rupturing device 601 in place with the body of the balloon 602 during an inflation or deflation. According to one embodiment, the balloon 602 and the rupturing device 601 may be encapsulated by a retractable sheath, similar to one shown in FIGS. 5A and 5B. The retractable sheath, when retracted, exposes the balloon 602 and the rupturing device 601 to the vulnerable plaque and places them against a fibrous cap of the vulnerable plaque.

Figure 7:
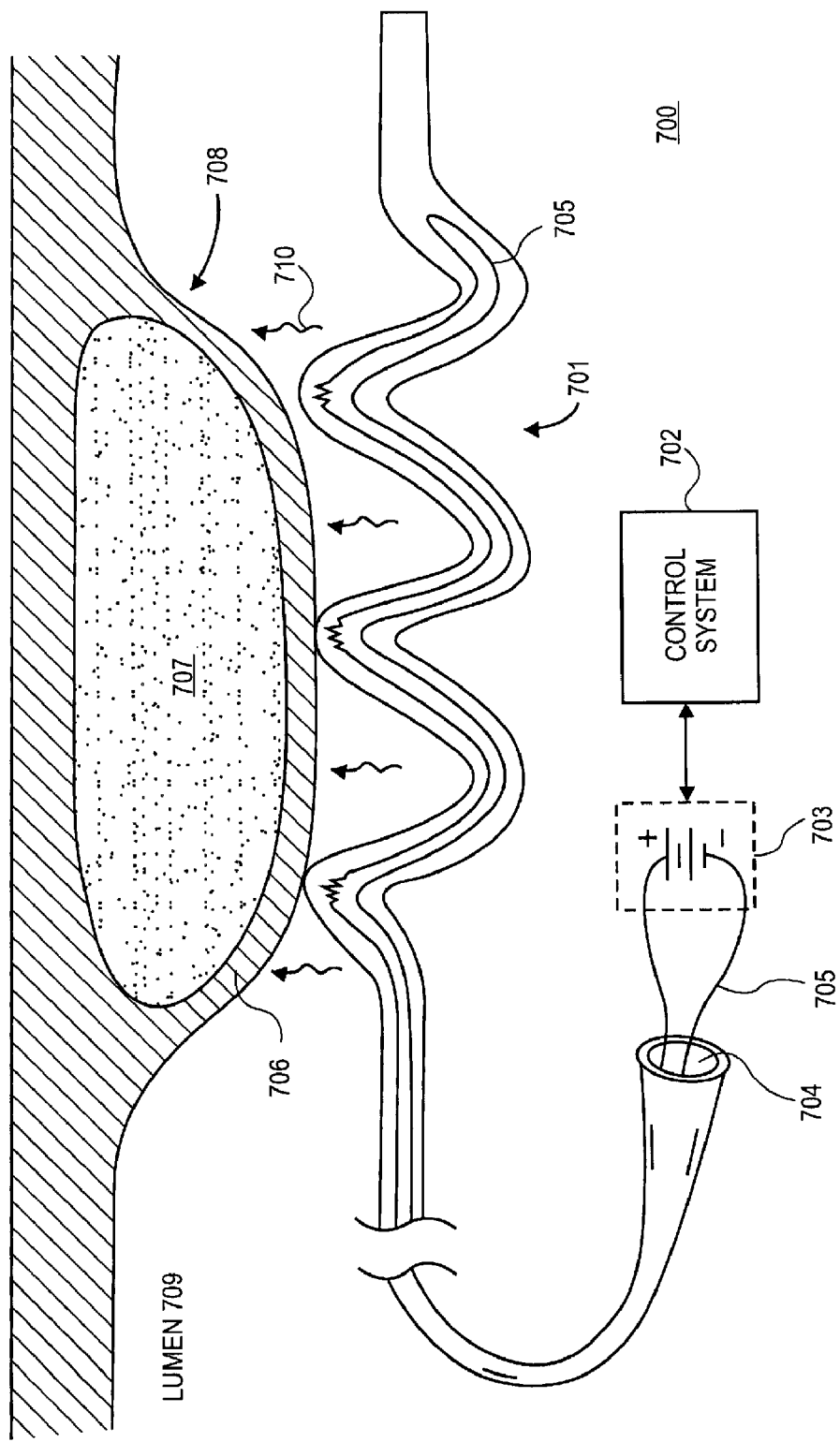
FIG. 7 is a diagram illustrating an exemplary system to treat a vulnerable plaque in accordance with one embodiment of the invention.

Studies find that a fibrous cap of a vulnerable plaque is easier to rupture when it is heated. Thus, it may be desirable to have the fibrous cap of a vulnerable plaque heated prior to or during the rupturing. FIG. 7 is a diagram illustrating a rupturing process with a heated vulnerable plaque in accordance with one embodiment of the invention. Referring to FIG. 7, in one embodiment, an exemplary system 700 includes a rupturing device 701 inserted into a body lumen 709 delivered by a catheter. The rupturing device 701 is then positioned against a fibrous cap 706 of vulnerable plaque 708 having a lipid pool 707. The rupturing device 701 may be positioned by an expandable device, such as a balloon or a stent. In addition, the rupturing device 701 further includes a lumen 704 within and throughout the rupturing device. An electrical wire 705 having a predetermined impedance is inserted into the lumen 704 to form an electrical circuit loop. A power supply 703 is coupled to the electrical loop from a proximal end of the catheter. The power supply 703 provides an electrical current flowing through the electrical wire 705 within the rupturing device 701. As a result, the electrical wire 705 with the predetermined impedance generates heat 710 along the rupturing device 701 which in turn heats up the fibrous cap 706 of the vulnerable plaque 708. When the vulnerable plaque 708 is heated up, the rupturing device 701 ruptures the fibrous cap 706 using one of the above methods and the contents of the lipid pool 707 may be drained thereafter.

In one embodiment, the rupturing device 701 is made of heat conductive biocompatible materials, such as stainless steel, such that the heat is easily transferred from the rupturing device 701 to the vulnerable plaque 708. It would be appreciated that other heating methods may be implemented. For example, a separate heating element may be provided and extended from a proximal end of the catheter to heat up the vulnerable plaque while the rupturing device ruptures the fibrous cap.

According to one embodiment, the power supply 703 is a programmable power supply which may be controlled by a control system 702. The control system 702 may be a computer. Alternatively, the control system 702 may be a part of IVUS system or OCT system shown in FIG. 2. In addition, the control system 702 may further include a temperature measuring subsystem (not shown), which connects to one or more thermal probes disposed along the rupturing device 701. The thermal probes may be used to detect the vulnerable plaque since the temperature of the vulnerable plaque is higher than an undiseased tissue. Alternatively, the thermal probes may be used to measure the temperature heating up the vulnerable plaque 708. As a result, the control system 702 may be able to constantly monitor the heating temperature of the area around the vulnerable plaque 708 to ensure the temperature is within a desirable range while the rupturing is performed. Other components apparent to one with ordinary skills in the art may be included.

As described above, the rupturing device may include a wire having a predefined shape or pattern to rupture a fibrous cap of a vulnerable plaque. In one embodiment, the simplest design of a predefined pattern is a straight wire, as shown in FIG. 8I. When placed on a vulnerable plaque with stress concentration, the wire ruptures a fibrous cap of the vulnerable plaque. According to another embodiment, as shown in FIG. 8A, a serpentine shaped wire stretches open during pulling to enhance rupturing the fibrous cap. In a further embodiment, a pattern with one or more protrusions orthogonal to each other may be used, such as ones shown in FIGS. 8B and 8C. In yet another embodiment, as shown in FIG. 8D, a pattern with a series of stress concentrations (e.g. enlarged dots) along a wire may be used. As shown in FIG. 8E, stress concentrations and serpentine shapes may be combined to form a rupturing device. Alternatively, as shown in FIG. 8F, one or more closed cells along a wire which open (to "grab"

portions of a fibrous cap) during pulling may be used. Other configurations or shapes, such as those shown in FIGS. 8G and 8H, may be used.

According to yet another embodiment of the invention, the rupturing device may include one or more sharp members disposed on a surface of an elongate member, as shown in FIG. 8J, to rupture a fibrous cap of a vulnerable plaque within a body lumen. Referring to FIG. 8J, according to one embodiment, the exemplary rupturing device 800 includes an elongate member 801 having a first surface and a second surface opposite to the first surface. One or more sharp members 802 are disposed on the first surface. Sharp members 802 are sharp enough, such that when sharp members 802 are placed against the fibrous cap of the vulnerable plaque, sharp members 802 can rupture the fibrous cap. Alternatively, the sharp members 802 may rupture the fibrous cap when they are pulled while being pushed against the fibrous cap. According to one embodiment, the second surface of the elongate member may be substantially smooth (e.g., substantially flat), such that an expandable device, such as a balloon or a stent, when expanded, may push on the second surface to force sharp members 802 against the fibrous cap while sharp members 802 are pulled, without disrupting the structure of the expandable device, as shown in FIG. 8K. Sharp members 802 may be made from wire, or cut from a flat or curved metal sheet or tube to provide the sharp edges. The device 800 may be disposed within a groove in the catheter so that the orientation of the surfaces (e.g. 802) are maintained properly. For example, a groove on a balloon lumen or on another structure within the catheter can maintain an orientation of the sharp side (sharp members 802) so that the sharp side faces outwardly rather than inwardly and the flat side faces inwardly (toward the balloon and balloon lumen).

Referring to FIG. 8K, according to one embodiment, the exemplary configuration 850 includes a rupturing device 852, which may be similar to rupturing device 800 shown in FIG. 8J, inserted into a body lumen 851 near a vulnerable plaque 854. Rupturing device 852 is then positioned against a fibrous cap of vulnerable plaque 854 by an expandable device 853. In this embodiment, expandable device 853 is an inflatable balloon. Alternatively, expandable device 853 may be an expandable stent. Rupturing device 852 may include one or more sharp members disposed on a first surface of an elongate member and the elongate member may include a substantially smooth second surface opposite to the first surface, similar to rupturing device 800 shown in FIG. 8J. Expandable device 853, when expanded, pushes on the second surface of rupturing device 852 to force the sharp members against the fibrous cap of vulnerable plaque 854. It is useful to note that the one or more sharp members may include sharp edges only facing a limited circumferential angle of the body lumen 851, instead of 360 degrees. As a result, the one or more sharp members of rupturing device 852 would not disrupt other members, such as expandable device 853. According to one embodiment, the one or more sharp members of rupturing device 852, when positioned against the fibrous cap of vulnerable plaque 854 by expandable device 853, rupture the fibrous cap. Alternatively, both rupturing device 852 and expandable device 853 are pulled to rupture the fibrous cap while the expandable device 853 maintains a stress concentration. Furthermore, rupturing device 852 may be pulled to rupture the fibrous cap while the expandable device 853 remains steady to maintain the stress concentration.

According to one embodiment, it is preferable to use a rupturing device with a balloon catheter during pretreatment. In addition, an intra-vascular ultrasonic (IVUS) system or an optical coherent tomography (OCT) system may be used to monitor the rupturing device and the fibrous cap during rupturing. The magnitudes of protrusions or amplitudes of the serpentine patterns may be made according to the degree of tearing desired. Furthermore, each of the above rupturing wires may include a lumen therein to allow an electrical wire to carry an electric current, similar to one shown in FIG. 7, to heat up a fibrous cap of a vulnerable plaque prior to or during the rupturing.

Figure 9:
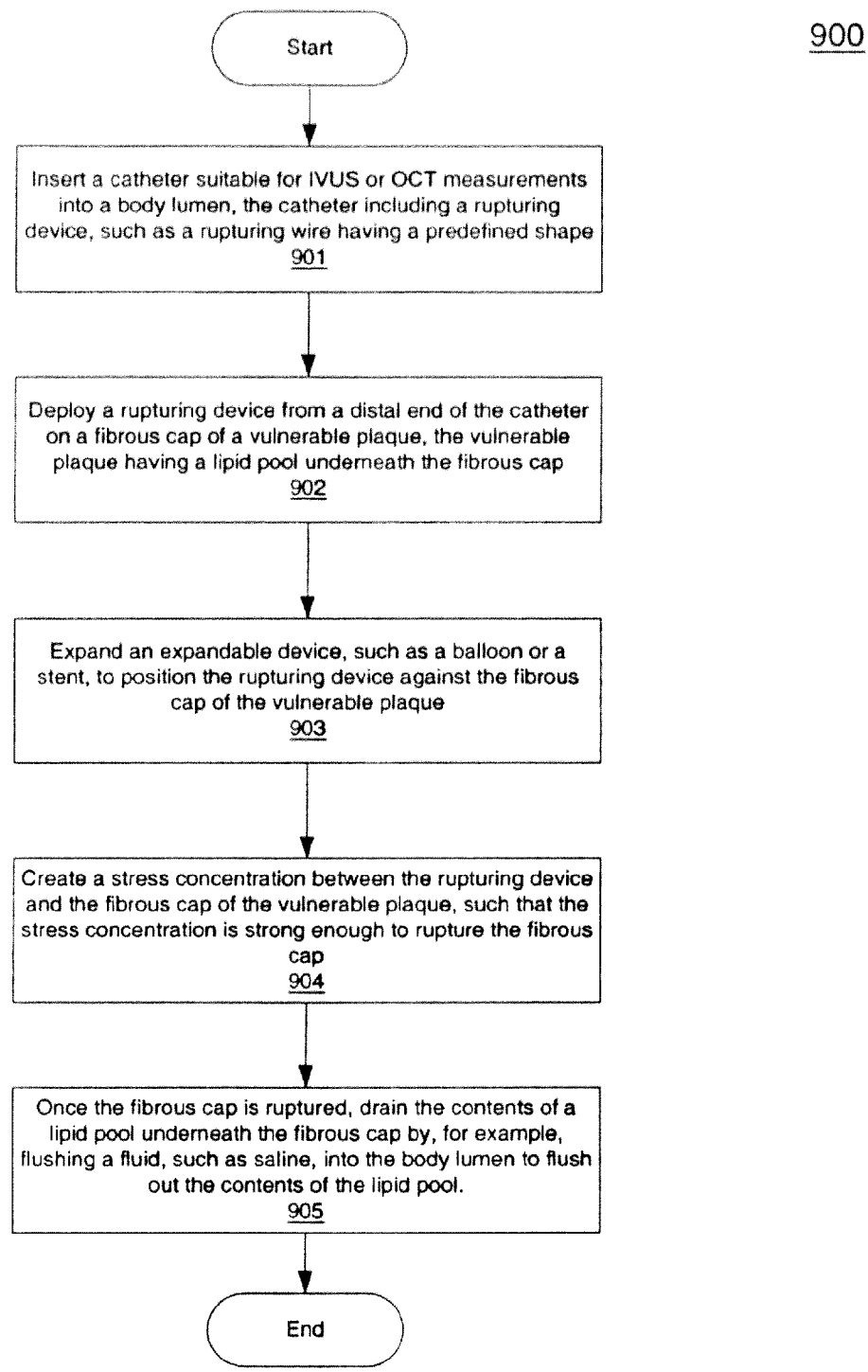
FIG. 9 is a flow diagram illustrating an exemplary process to rupture a fibrous cap of a vulnerable plaque, according to one embodiment of the invention.

FIG. 9 is flow diagram illustrating an exemplary rupturing process in accordance with one embodiment of the invention. Referring to FIG. 9, the exemplary process 900 includes positioning a rupturing device against a vulnerable plaque and rupturing a fibrous cap of the vulnerable plaque through the rupturing device.

Referring to FIG. 9, at block 901, a catheter suitable for an imaging system, such as an IVUS or an OCT measurements, is inserted into a body lumen. The catheter may include a rupturing device disposed at a distal end of the catheter, such as a rupturing wire having a predefined shape (e.g., similar to those shown in FIGS. 8A to 8J). The imaging system and the rupture system may be separate devices. At block 902, the rupturing device is deployed and placed on a fibrous cap of a vulnerable plaque. The vulnerable plaque may include a lipid pool underneath the fibrous cap. At block 903, an expandable device, such as a balloon or a stent, is deployed which positions the rupturing device against the fibrous cap of the vulnerable plaque. As a result, at block 904, a stress concentration is created between the rupturing device and the fibrous cap of the vulnerable plaque. According to one embodiment, the stress concentration is strong enough that the fibrous cap is ruptured by the rupturing device. Once the fibrous cap is ruptured, at block 905, the contents of the lipid pool underneath the fibrous cap is drained by, for example, flushing a fluid, such as saline or heparinized saline, into the body lumen to flush out the contents of the lipid pool.

Figure 10:
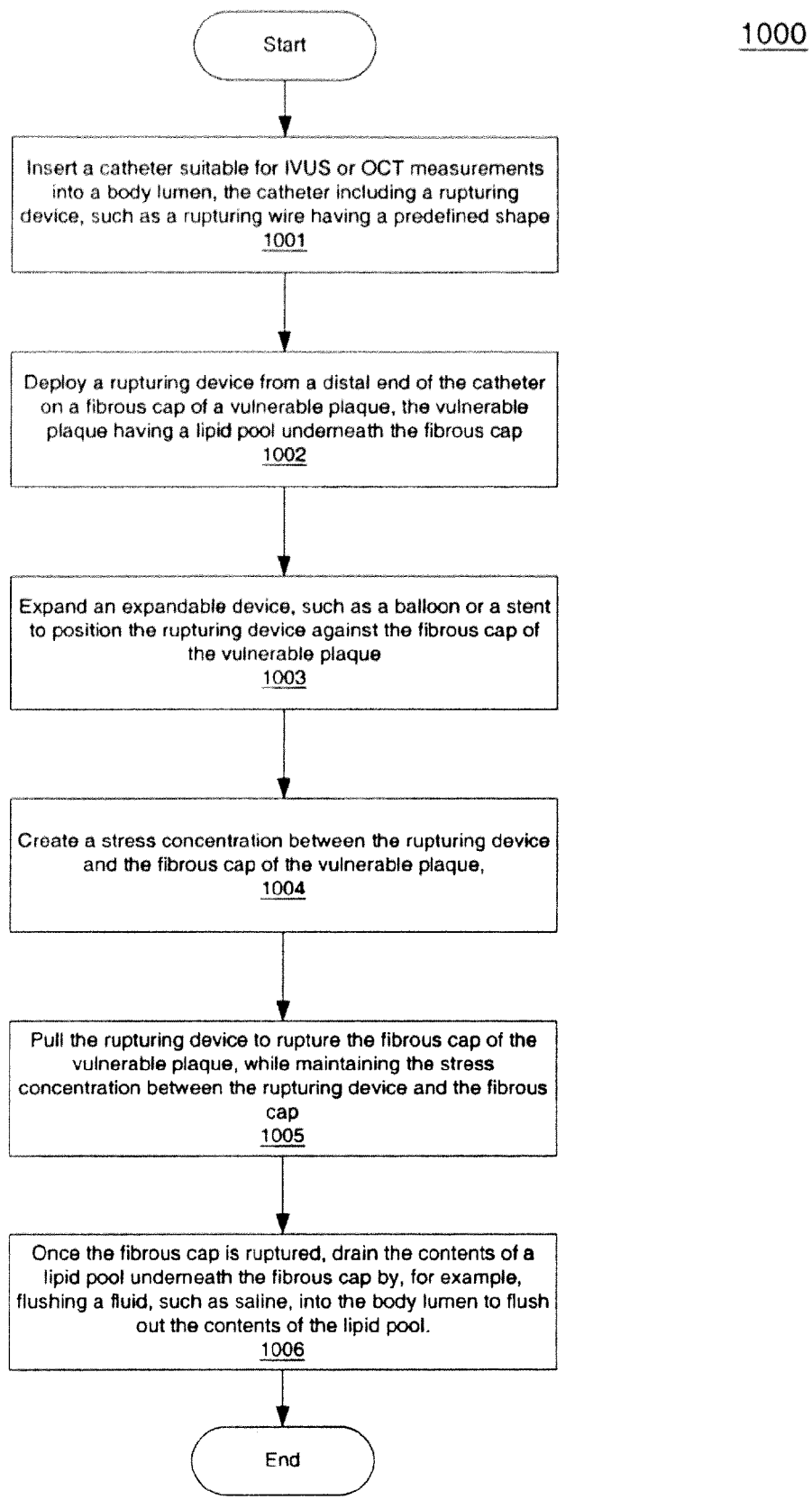
FIG. 10 is a flow diagram illustrating an exemplary process to rupture a fibrous cap of a vulnerable plaque, according to another embodiment of the invention.

FIG. 10 is a diagram illustrating an exemplary rupturing process in accordance with another embodiment of the invention. Referring to FIG. 10, after a vulnerable plaque is detected via one of the above methods (e.g., using IVUS or OCT system, or temperature measurement), at block 1001, a catheter suitable for IVUS or OCT is inserted into a body lumen. The catheter may include a rupturing device disposed at a distal end of the catheter. In one embodiment, the rupturing device may be a rupturing wire having a predefined shape or pattern, such as those shown in FIGS. 8A to 8I. At block 1002, the rupturing device is deployed from the distal end of the catheter.

According to one embodiment, the catheter may include both temperature detection capability and rupturing functionality. As a result, a catheter may be used to detect a vulnerable plaque by detecting a temperature of the vulnerable plaque through one or more thermal sensors deployed from a distal end of the catheter. In one embodiment, each of the thermal sensors deployed may include a flow deflector to deflect a fluid flow (e.g., a blood flow) away from the respective region being detected to further improve an accuracy of the measurement. Once the vulnerable plaque is detected, the catheter may deploy a rupturing device from the distal end to rupture a fibrous cap of the vulnerable plaque. In addition, the catheter may be suitable for IVUS or OCT measurements, such that the detection of the vulnerable plaque and rupturing of a fibrous cap of the vulnerable plaque may be monitored by either an IVUS or an OCT system.

At block 1003, an expandable device is expanded to position the rupturing device against the fibrous cap of the vulnerable plaque. In one embodiment, the expandable device is an inflatable device, such as a balloon. Alternatively, the expandable device may be a stent which may be deployed during a stenting procedure. Other expandable devices may be utilized. In one embodiment, during a delivery of the catheter into the body lumen, both rupturing device and the expandable device are encapsulated within a retractable sheath of the catheter. Once the catheter is delivered, the retractable sheath is retracted to expose and position the rupturing device against the vulnerable plaque via the expandable device. As a result, at block 1004, a stress concentration is created between the expandable device and the fibrous cap of the vulnerable plaque. In one embodiment, the stress concentration is strong enough to enable the rupturing device to rupture the fibrous cap of the vulnerable plaque.

In one embodiment, if the stress concentration is not strong enough to allow the rupturing device to rupture the fibrous cap of the vulnerable plaque, at block 1005, the rupturing device is pulled to rupture the fibrous cap while the expandable device maintains the stress concentration between the rupturing device and the fibrous cap. The rupturing device may be a rupturing wire having one of the predetermined shapes or patterns defined in FIGS. 8A to 8I. As a result, a predetermined shape (e.g., one of those shown in FIGS. 8A to 8I), in combination with the stress concentration between the rupturing device and the fibrous cap created through the expandable device, enables the rupturing device to rupture the fibrous cap when the rupturing device is pulled.

Once the fibrous cap of the vulnerable plaque is ruptured, at block 1006, contents of a lipid pool underneath the fibrous cap are drained. In one embodiment, a fluid, such as saline or heparinized saline, is flushed into the body lumen to flush out the contents of the lipid pool. In one embodiment, a fluid is infused into the body lumen through a flush lumen within the catheter and exits via a port disposed at a distal end of the catheter, to flush out the contents of the lipid pool. Other configurations may be utilized.

Figure 11:
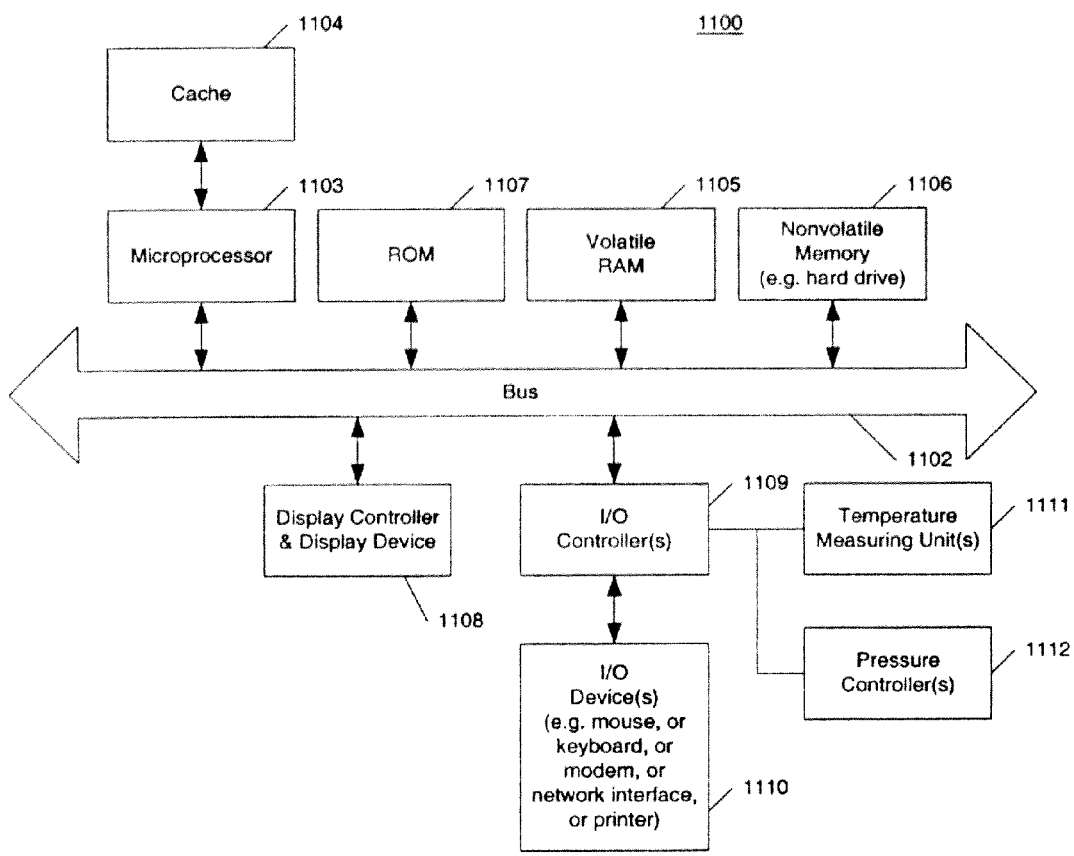
FIG. 11 is block diagram illustrating an exemplary computer system which may be used with one embodiment of the invention.

FIG. 11 shows a block diagram of an exemplary computer, which may be used with one embodiment of the invention, such as the imaging system 201 of FIG. 2. Alternatively, system 1100 may be a computer system embedded within after loader 202. Furthermore, system 1100 may be a part of the control system 702 of FIG. 7. Note that while FIG. 11 illustrates various components of a computer system, it is not intended to represent any particular architecture or manner of interconnecting the components, as such details are not germane to the present invention. It will also be appreciated that network computers and other data processing systems or communication devices/systems, which have fewer components or perhaps more components, may also be used with the present invention.

As shown in FIG. 11, the computer system 1100, which is a form of a data processing system, includes a bus 1102 which is coupled to a microprocessor 1103 and a ROM 1107, a volatile RAM 1105, and a non-volatile memory 1106. The microprocessor 1103, which may be a PowerPC G3 or PowerPC G4 microprocessor from Motorola, Inc. or IBM, is coupled to cache memory 1104 as shown in the example of FIG. 11. The bus 1102 interconnects these various components together and also interconnects these components 1103, 1107, 1105, and 1106 to a display controller and display device 1108, as well as to multimedia device 1111 including an audio device and to peripheral devices such as input/output (I/O) devices, which may be mice, keyboards, modems, network interfaces, printers, and other devices which are well-known in the art. Typically, the input/output devices 1110 are coupled to the system through input/output controllers 1109. The volatile RAM 1105 is typically implemented as dynamic RAM (DRAM) which requires power continuously in order to refresh or maintain the data in the memory. The non-volatile memory 1106 is typically a magnetic hard drive, a magnetic optical drive, an optical drive, or a DVD RAM or other type of memory systems which maintain data even after power is removed from the system. Typically the non-volatile memory will also be a random access memory, although this is not required. The bus 1102 may include one or more buses connected to each other through various bridges, controllers, and/or adapters, as is well-known in the art. In one embodiment, the I/O controller 1109 includes a USB (Universal Serial Bus) adapter for controlling USB peripherals.

In one embodiment, the system 1100 further includes one or more temperature measuring units 1111 coupled to an I/O controller 1109 for measuring the temperature of vulnerable plaque of a vessel wall through a thermography device. The temperature measuring unit 1111 may include a temperature control subsystem, such as the control system 702 of FIG. 7 to control the temperature to heat up a fibrous cap of a vulnerable plaque during a rupturing procedure. In one embodiment, the system 1100 may include a pressure controller 1112 for controlling a pressure to inflate or deflate a balloon, such as the balloon 303 of FIGS. 3A and 3B to position a rupturing device against a fibrous cap of a vulnerable plaque. In addition, the temperature measuring unit 1111 and pressure controller 1112 may be coupled to the network interface 1110 through a network, such as local area network (LAN). Other networks, such as wide area network (WAN) or Internet, may be utilized. Other configurations may exist.

It will be appreciated that the various rupturing devices described herein may be used with a variety of different medical intervention devices. For example, these various rupturing devices may be used in balloon angioplasty catheters or guidewire catheters or stent delivery catheters or drug delivery catheters or radiation delivery catheters, etc. These various catheters will often include numerous lumens such as guidewire lumen, a balloon inflation lumen (e.g. to inflate an angioplasty or centering balloon), a perfusion lumen, a drug delivery lumen, etc. In addition, in those embodiments which use an external pressure controller, an additional lumen, such as a hydraulic pressure lumen (to transmit a pressure from the controller with a proximal end of the catheter to a pressure sensitive device at a distal end), is included in such catheters. Other types of medical intervention devices may use the various markers described herein.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A medical device comprising:
  a catheter shaft;
  an elongated rupturing wire deliverable through the catheter shaft and having a predefined shape adapted to rupture a fibrous cap of a vulnerable plaque, wherein the fibrous cap is ruptured when the elongated rupturing wire is pulled against the vulnerable plaque, and
  an expandable holding device configured to hold the elongated rupturing wire against the vulnerable plaque when in an expanded configuration outside of the catheter shaft;
  wherein the elongated rupturing wire is not integrally formed with the expandable holding device and when the expandable holding device is in the expanded configuration outside of the catheter shaft a continuous length of the elongated rupturing wire extends both within the catheter shaft and adjacent an outer surface of the expandable holding device such that the elongated rupturing wire is movable relative to the outer surface of the expandable holding device, along an axis of the expandable holding device while the outer surface of expandable holding device is in direct contact with and applies pressure to the elongated rupturing wire laterally with respect to the axis.

2. The apparatus of claim 1, wherein the catheter shaft is a part of a catheter suitable for intra-vascular ultrasonic (IVUS) or optical coherent tomography (OCT) measurements.

3. The apparatus of claim 1, wherein the elongated rupturing wire ruptures the fibrous cap of the vulnerable plaque while the expandable holding device holds the elongated rupturing wire against the vulnerable plaque and the elongated rupturing wire is moved from a position distal of a proximal end of the expandable holding device to a position which is proximal to a proximal end of the expandable holding device.

4. The apparatus of claim 1, wherein the expandable holding device, when in the expanded configuration outside of the catheter shaft, positions the elongated rupturing wire against the vulnerable plaque and the elongated rupturing wire is moved from a position distal of a proximal end of the expandable holding device to a position which is proximal to a proximal end of the expandable holding device.

5. The apparatus of claim 4, wherein the fibrous cap is ruptured when the elongated rupturing wire along with the expandable holding device is pulled against the vulnerable plaque.

6. The apparatus of claim 4, wherein the fibrous cap is ruptured when the elongated rupturing wire is pulled while the expandable holding device remains steady to hold the elongated rupturing wire against the vulnerable plaque.

7. The apparatus of claim 4, wherein the expandable holding device comprises a balloon and wherein when inflated, the balloon positions the elongated rupturing wire against the vulnerable plaque.

8. The apparatus of claim 4, wherein the expandable holding device comprises a stent and wherein when deployed, the stent positions the elongated rupturing wire against the vulnerable plaque.

9. The apparatus of claim 4, wherein the expandable holding device, when in the expanded configuration outside of the catheter shaft, creates a stress concentration between the elongated rupturing wire and the vulnerable plaque, and wherein the stress concentration ruptures the fibrous cap.

10. The apparatus of claim 1, wherein the predefined shape includes a shape selected from the group consisting of:
   a serpentine shape;
   one or more protrusions orthogonal to each other;
   a series of stress concentrations along the wire;
   a senate pattern;
   a serpentine shape with a series of stress concentrations; and
   one or more closed cells.

11. The apparatus of claim 1, wherein the elongated rupturing wire comprises a lumen having an electrical wire therein and wherein an electric current flowing within the electrical wire generates a heat to heat up the vulnerable plaque.

12. The apparatus of claim 1, further comprising a draining device to drain a lipid pool of the vulnerable plaque when the fibrous cap is ruptured.

13. The apparatus of claim 1, wherein a lipid pool is substantially embedded within a wall of the body lumen under the fibrous cap.

14. The apparatus of claim 13, wherein the lipid content is released into the body lumen when the fibrous cap is ruptured without removing the lipid pool from the wall of the body lumen.

15. A catheter, comprising:
   a catheter shaft;
   a retractable elongated rupturing wire having a predefined shape extendable through the catheter shaft from a distal end of the catheter shaft; and
   an expandable device extendable from the distal end of the catheter;
   wherein the expandable device is adapted to position the elongated rupturing wire against a vulnerable plaque to rupture a fibrous cap of the vulnerable plaque when in an expanded configuration outside of the catheter shaft, the elongated rupturing wire is not integrally formed with the expandable device, and when the expandable device is in the expanded configuration outside of the catheter shaft a continuous length of the elongated rupturing wire extends both within the catheter shaft and adjacent an outer surface of the expandable device such that the elongated rupturing wire is movable relative to the outer surface of the expandable device along an axis of the expandable device, while the outer surface of the expandable device is in direct contact with and applies pressure to the elongated rupturing wire laterally with respect to the axis.

16. The catheter of claim 15, further comprising a retractable sheath for encapsulating the elongated rupturing wire and the expandable device, wherein the retractable sheath, when retracted, exposes the elongated rupturing wire and the expandable device to the vulnerable plaque.

17. The catheter of claim 16, wherein the retractable sheath, when retracted, expands the expandable device which positions the elongated rupturing wire against the vulnerable plaque.

18. The apparatus of claim 15, wherein the expandable device comprises a balloon and wherein when inflated, the balloon positions the elongated rupturing wire against the vulnerable plaque.

19. The apparatus of claim 15, wherein the expandable device comprises a stent and wherein when deployed, the stent positions the elongated rupturing wire against the vulnerable plaque.

20. The apparatus of claim 15, wherein the predefined shape includes a shape selected from the group consisting of:
   a serpentine shape;
   one or more protrusions orthogonal to each other;
   a series of stress concentrations along the wire;
   a senate pattern;
   a serpentine shape with a series of stress concentrations; and
   one or more closed cells.

21. The catheter of claim 15, wherein a lipid pool is substantially embedded within a wall of a body lumen under the fibrous cap.

22. The catheter of claim 21, wherein the lipid content is released into the body lumen when the fibrous cap is ruptured without removing the lipid pool from the wall of the body lumen.

23. An apparatus, comprising:
   an expandable device;
   a retractable elongated rupturing wire having a proximal portion, a distal portion, and an intermediate portion between the proximal and distal portions, wherein the elongated rupturing wire is movable relative to the expandable device along an axis of the expandable device; and at least one sharp member disposed on a surface of the elongated rupturing wire along the intermediate portion of the elongated rupturing wire;

wherein the at least one sharp member is adapted to rupture a fibrous cap of a vulnerable plaque when the at least one sharp member is positioned and pulled against the vulnerable plaque, wherein an outer surface of the expandable device, when expanded, is in direct contact with and pushes the elongated rupturing wire laterally with respect to the axis of the expandable device to position the at least one sharp member against the fibrous cap of the vulnerable plaque to rupture the fibrous cap, and the at least one sharp member is movable from a position distal of a proximal end of the expandable device to a position which is proximal to a proximal end of the expandable device, when expanded.

24. The apparatus of claim 23, wherein the at least one sharp member includes a sharp edge formed from a metal sheet.

25. The apparatus of claim 23, wherein the elongated rupturing wire further comprises a second surface opposite to the first surface, the second surface being substantially smooth.

26. The apparatus of claim 25, wherein the second surface is pushed by the expandable device, when expanded, to position and push the at least one sharp member against the fibrous cap of the vulnerable plaque to rupture the fibrous cap.

27. The apparatus of claim 26, wherein the expandable device is an inflatable balloon or a stent.

28. The apparatus of claim 26, wherein the elongated rupturing wire along with the at least one sharp member are pulled to rupture the fibrous cap while the expanded device pushes on the second surface to maintain a stress concentration between the sharp member and the fibrous cap.

29. The apparatus of claim 23, wherein a lipid pool is substantially embedded within a wall of a body lumen under the fibrous cap.

30. The apparatus of claim 29 wherein the lipid content is released into the body lumen when the fibrous cap is ruptured without removing the lipid pool from the wall of the body lumen.

31. An apparatus, comprising:

a catheter shaft;

an elongated rupturing wire for rupturing a vulnerable plaque having a lipid pool;

means for delivering the elongated rupturing wire to a location of the vulnerable plaque;

means for positioning the elongated rupturing wire against the vulnerable plaque; and means for moving the elongated rupturing wire relative to the positioning means along an axis of the positioning means to release lipid content from the lipid pool of the vulnerable plaque;

wherein when the positioning means is in an expanded configuration outside of the catheter shaft a length of the elongated rupturing wire extends both within the catheter shaft and adjacent an outer surface of the positioning means such that the elongated rupturing wire is movable from a position distal of a proximal end of the positioning means to a position which is proximal to a proximal end of the positioning means while the outer surface of the positioning means is in direct contact with and pushes the elongated rupturing wire against the fibrous cap laterally with respect to the axis of the positioning means.

* * * * *